United States Patent

Ruby et al.

[11] Patent Number: 5,324,644
[45] Date of Patent: Jun. 28, 1994

[54] PROCESS FOR PRODUCING IMMUNOSUPPRESSANT AGENT

[75] Inventors: Carolyn L. Ruby, Montclair; Christine C. Chung, Edison; Byron H. Arison, Watchung, all of N.J.

[73] Assignee: Merck & Co., Inc., Rahway, N.J.

[21] Appl. No.: 920,958

[22] Filed: Jul. 28, 1992

[51] Int. Cl.$^5$ .................. C12P 17/18; C12P 7/00; C12P 7/24; C12P 7/02

[52] U.S. Cl. ............................. 435/119; 435/132; 435/147; 435/155; 435/170

[58] Field of Search ............ 435/119, 170, 886, 253.5, 435/132, 147, 155

[56] References Cited

U.S. PATENT DOCUMENTS

| | | | |
|---|---|---|---|
| 3,094,460 | 6/1963 | DeBoer et al. | 424/118 |
| 3,244,592 | 5/1966 | Arai | 424/115 |
| 4,981,792 | 1/1991 | Inamin et al. | 435/119 |

FOREIGN PATENT DOCUMENTS

| | | |
|---|---|---|
| 1151091 | 8/1983 | Canada . |
| 0184162 | 2/1986 | European Pat. Off. . |
| 0349061A2 | 1/1990 | European Pat. Off. . |
| 0353678A2 | 2/1990 | European Pat. Off. . |

OTHER PUBLICATIONS

J. Antibiotics, 15, pp. 231–232 (1962), by T. Arai, et al., entitled *Ascomycin, an Antifungal Antibiotic*.

Seiichi et al., Chemical Abstracts, 116(11): 104486t, 1992.

*Primary Examiner*—Douglas W. Robinson
*Assistant Examiner*—Maria L. Osoteo
*Attorney, Agent, or Firm*—Charles M. Caruso; J. Eric Thies

[57] ABSTRACT

Described is a new process for producing the immunosuppressant, L-682,993, a C-31 demethylated derivative of L-679,934 (FK-506), produced under fermentation conditions utilizing the new mutant microorganism Streptomyces sp. (Merck Culture Collection MA 7017) ATCC No. 55334, being a blocked second generation mutant of Streptomyces sp. (MA 6858) ATCC No. 55098. The macrolide immunosuppressant is useful in preventing human host rejection of foreign organ transplants, e.g. bone marrow and heart transplants.

1 Claim, 2 Drawing Sheets

L-682,993

PROCESS FOR PRODUCING IMMUNOSUPPRESSANT AGENT

BACKGROUND OF THE INVENTION

1. Field of the Invention

This invention relates to a novel process for producing the immunosuppressant agent L-682,993, also described as 31-desmethoxy-31-hydroxy-FK-506, using the new mutant microorganism Streptomyces sp. (MA 7017) ATCC No. 55334, being a blocked second generation mutant of Streptomyces sp. MA 6858. The process involves culturing the new microorganism under aerobic fermentation conditions in an aqueous carbohydrate medium containing a nitrogen nutrient.

2. Brief Description of Disclosures in the Art

In 1983, the US FDA approved Cyclosporin A, an extremely effective anti-rejection drug that revolutionized the field of organ transplant surgery. The drug acts by inhibiting the body's immune system from mobilizing its vast arsenal of natural protecting agents to reject the transplant's foreign protein.

As effective as the drug is in fighting transplantation rejection, it suffers drawbacks in causing kidney failure, liver damage, and ulcers which in many cases can be severe.

EPO Publication No. 0184162 to Fujisawa, hereby incorporated by reference, describes a new macrolide immunosuppressant FK-506 (FR-900506) which is reputed to be 100 times more effective than cyclosporin A. The macrolide is produced by fermentation of a particular strain of Streptomyces tsukubaensis. Also described is the closely related macrolide immunosupressant FK-520 (FR-900520), produced by S. hygroscopicus subsp. yakushimaensis.

EPO 0 349 049 (assigned to Merck & Co., Inc.) published Jan. 3, 1990, now U.S. Pat. No. 4,981,792, describes a biotransformation process for producing C-31 desmethyl FK-506, utilizing the microorganism ATCC No. 53711 in the presence of L-679,934 (FK-506) to effect a biotransformation of L-679,934. However a direct fermentation process for producing C-31 desmethyl FK-506 is not described.

EPO 0 388 152 (assigned to Merck & Co., Inc.) published Sep. 19, 1990, describes a new process for the direct fermentation production of C-31 demethylated FK-520 (FR-900520) utilizing the microorganism ATCC No. 53855. However the process is not applicable for the fermentation of C-31 demethylated FK-506.

PCT WO 89/05304 to Fisons, published Jun. 15, 1989, also discloses C-31 desmethyl FK-506, but does not describe or suggest a method of preparation.

Processes for producing C-31 desmethyl FK-506 directly by fermentation of a microorganism, rather than a biotransformation requiring FK-506 as a substrate, are highly desired in the field.

BRIEF DESCRIPTION OF THE FIGURE

The FIG. 1A represents the proton nuclear magnetic spectrum of C-31 desmethyl FK-506, (L-682,993) also known as "demethomycin" together with its assigned molecular structure (FIG. 1B) and our particular numbering system. The formal chemical name used by Fujisawa for this structure is: 17-allyl-1,14-dihydroxy-12-[2'-(3'',4''-dihydroxy-cyclohexyl)-1'-methylvinyl]-23,25-dimethoxy-13,19,21,27-tetramethyl-11,28-dioxa-4-azatricyclo-[22.3.1.0$^{4,9}$]-octacos-18-ene-2,3,10,16-tetraone. Note that in our numbering system, Fujisawa's 17-allyl becomes 21-allyl, 3'' becomes C-31, and 4'' becomes C-32.

SUMMARY OF THE INVENTION

Figure 1A:
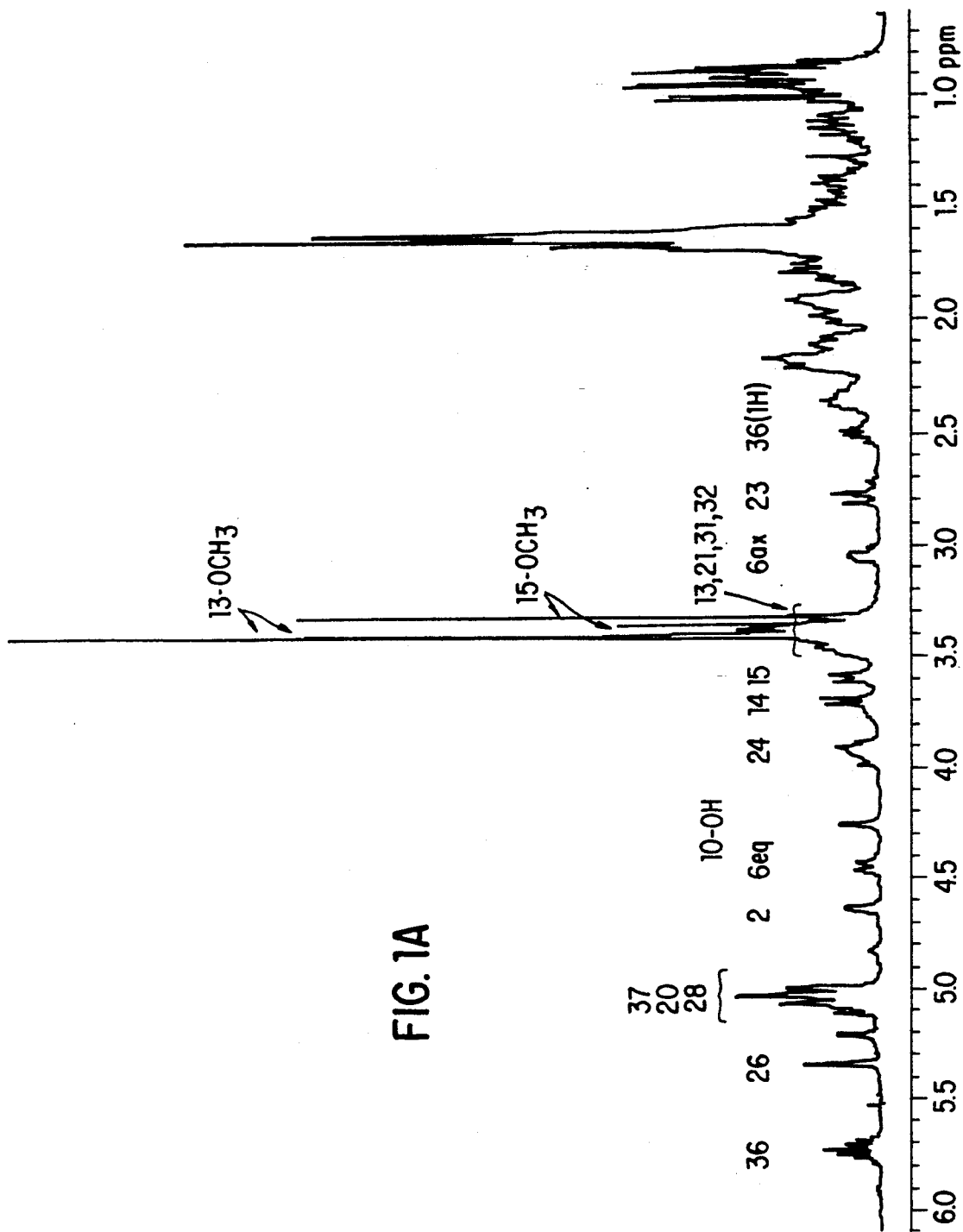
Figure 1B:
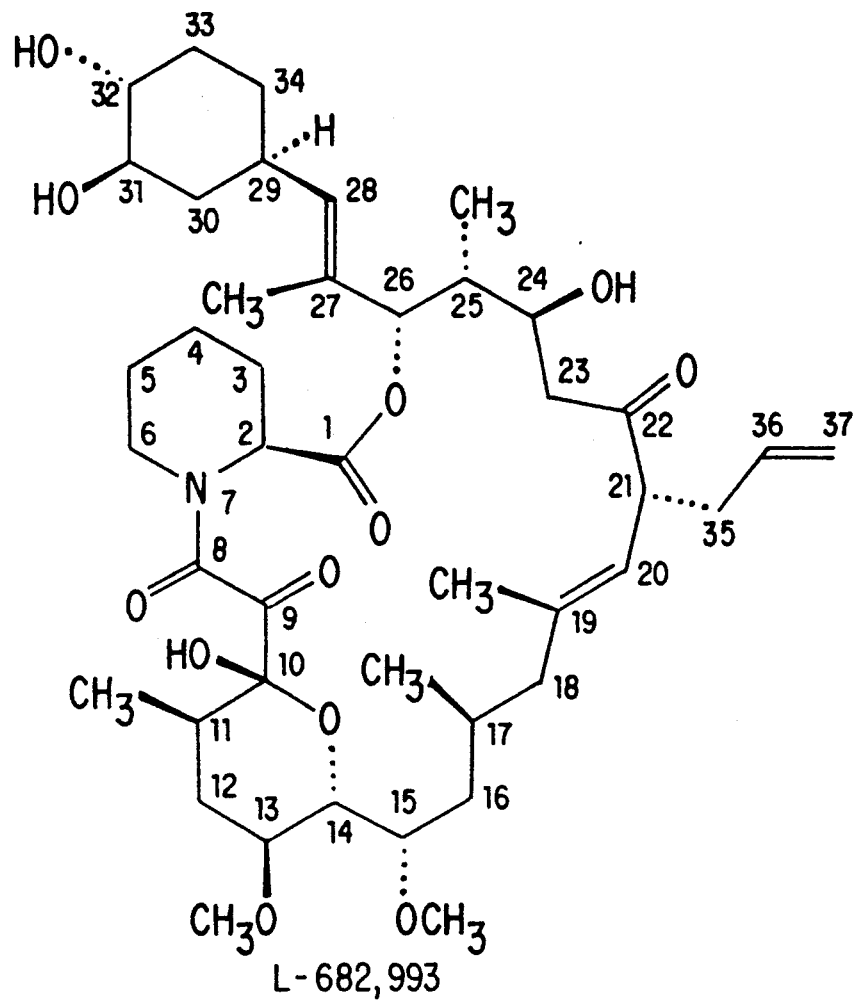

It has been found that the immunosuppressant, L-682,993, can be directly obtained by the fermentation of the mutant microorganism Streptomyces sp. (MA 7017) ATCC No. 55334, which mutant is derived from a first generation mutant of MA 6858 by the mutagenic treatment of N-methyl-N'-nitro-N-nitrosoguanidine. The fermentation does not require the presence of the macrolide immunosuppressant FK-506, and is conducted under submerged aerobic conditions in an aqueous carbohydrate medium, containing a nitrogen nutrient, said conditions being conducted at a pH of about 7, for a sufficient time to produce L-682,993.

The resultant L-682,993 exhibits immunosuppressive activity, i.e., positive inhibition of T-cell activation, as demonstrated by the calcium ionophore (ionomycin) plus phorbol myristate acetate (PMA) induced T-cell stimulation assay, also referred to herein as the "T-cell proliferation assay". (See F. Dumont et al., J. Immunology, Vol. 144, p. 251–258, (1990). The principle of this assay is to measure the proliferation of mouse T lymphocytes stimulated with the combination of ionomycin plus PMA. A positive sample in this assay will inhibit T-cell proliferation, as indicated by reduced tritiated thymidine uptake.

In accordance with this invention, there is provided a process for producing the immunosuppressant, identified as L-682,993 (demethomycin), comprising the step of culturing a strain of a mutant of Streptomyces sp. MA 7017, ATCC No. 55334, under submerged aerobic fermentation conditions in an aqueous carbohydrate medium containing a nitrogen nutrient for a sufficient time to produce product L-682,993 (demethomycin).

Also provided is the unfiltered broth produced by the above process. In addition, there is provided a new mutant microorganism, Streptomyces sp. ATCC No. 55334.

DETAILED DESCRIPTION OF THE INVENTION AND PREFERRED EMBODIMENTS

The present invention involves the fermentation of Streptomyces sp. ATCC No. 55334 to produce L-682,993. The microorganism is currently on deposit filed Jun. 24, 1992, with the American Type Culture Collection, 12301 Parklawn Drive in Rockville, Md. as ATCC No. 55334, and in the Merck Culture Collection in Rahway, N.J. as MA 7017. The physical characteristics and taxonomy, including morphological, cultural, biological and physiological characteristics are briefly described herein below.

The Streptomyces sp. strain MA 7017 grows very slowly on agar media and a preferred growth medium is one fourth strength Yeast Malt Extract Agar at 27 degrees Celsius.

The present invention process can be practiced with any L-682,993-producing strain of Streptomyces sp., and particularly preferred is the herein described mutant ATCC No. 55334.

In general, L-682,993 can be produced by culturing (fermenting) the above-described mutant strain in an aqueous nutrient medium containing sources of assimilable carbon and nitrogen, preferably under submerged aerobic conditions (e.g. shaking culture, submerged culture, etc.). The aqueous medium is preferably maintained at a pH of about 7 at the initiation and termination (harvest) of the fermentation process. A higher pH leads to substantial and/or total loss of product. The desired pH may be maintained by the use of a buffer such as morpholinoethanesulfonic acid (MES), morpholinopropanesulfonic acid (MOPS), and the like, or by choice of nutrient materials which inherently possess buffering properties, such as production media described hereinbelow.

The preferred sources of carbon in the nutrient medium are carbohydrates such as glucose, xylose, ribose, galactose, glycerin, starch, dextrin, and the like. Other sources which may be included are maltose, rhanmose, raffinose, arabinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic salts (e.g. ammonium nitrate, ammonium sulfate, ammonium phosphate, etc.,), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

As to the conditions for production of L-682,993 in massive amounts, submerged aerobic cultural conditions are preferred therefor. For the production of small amounts, a shaking or surface culture in a flask, bottle or culture dish is employed. Furthermore, when the growth is carried out in large tanks, it is preferable to use the vegetative form of the organism for inoculation in the production tanks in order to avoid growth lag in the process of production of L-682,993. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is substantially the same as or different from the medium utilized for the production of L-682,993 and is generally autoclaved to sterilize the medium prior to inoculation. The pH of the medium is generally adjusted to about 7 prior to the autoclaving step by suitable addition of an acid or base, preferably in the form of a buffering solution.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the fermentation mixture.

The fermentation is usually conducted at a temperature between about 20° C. and 40° C., preferably 25°-35° C., for a period of 48 hours to 168 hours, which may be varied according to fermentation conditions and scales. Preferably, the production cultures are incubated for about 168 hours at 25° C. on a rotary shaker operating at 220 rpm, wherein the pH of the fermentation medium is maintained at 7 to harvest.

Preferred culturing/production media for carrying out the fermentation include the following:

|  | g/L |
|---|---|
| Seed Medium A | |
| $KNO_3$ | 2.0 |
| Glucose | 20.0 |
| Yeast extract | 20.0 |
| HyCase SF | 20.0 |
| $FeSO_4.7H_2O$ | 0.025 |
| NaCl | 0.5 |
| $MgSO_4.7H_2O$ | 0.5 |
| $MnSO_4.7H_2O$ | 0.005 |
| $ZnSO_4.7H_2O$ | 0.01 |
| $CaCl_2.2H_2O$ | 0.02 |
| Adjust pH to 7.0. | |
| Production Medium B | |
| Ardamine PH | 30.0 |
| MOPS | 10.0 |
| Glucose | 75.0 |
| $CaCO_3$ | 1.0 |
| Adjust pH to 6.8. | |

The produced L-682,993 can be recovered from the culture medium by conventional means which are commonly used for the recovery of ether known biologically active substances. The L-682,993 substance produced is found in the cultured mycelium and filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methanol and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred method is solvent extraction, particularly using methanol.

The product L-682,993 from the fermentation exhibits positive immunosuppressive activity y the "T-cell proliferation assay" and possesses utility on this basis.

The following examples are given for the purpose of illustrating the present invention and should not be construed as being limitations on the scope or spirit of the instant invention.

EXAMPLE I

Mutagenesis and Culture Conditions

Spores of MA 6959 are prepared from ¼YME agar (Difco yeast extract, 0.1%, malt extract, 0.25%, glucose 0.1%, pH adjusted to 7.0 and agar, 1.5%) and are incubated in TM-buffer (0.05M Tris, 0.05M maleic acid adjusted to pH 9 with NAOH) containing N-methyl-N'-nitro-N-nitrosoguanidine at a concentration of 2 mg/ml. Incubation is at room temperature with gentle agitation for 8 hours. The treated spores are plated for isolated colonies on ¼YME agar. Methanol extracts of fermentations of these colonies are examined by thin layer chromatography (TLC) for mutant phenotypes. The subject mutant, MA 7017, was identified as an isolate which produces a major component which is more polar than the major parent compound (L-679,934) in the solvent system of chloroform:methanol (9:1). Confirmation of the mutant phenotype is obtained by fermentation, extraction and TLC and HPLC analyses of reisolates of the original colony "patch". The fermentation involves inoculating a 250 ml baffled Erlenmeyer flask containing 50 ml of an autoclaved seed medium prepared with distilled water and consisting of $KNO_3$, 0.2%, HyCase SF, 2%, Difco yeast extract, 2%, glucose, 2%, $FeSO_4.7 H_2O$, 0.0025%, NaCl. 0.05%, $MgSO_4.7 H_2O$, 0.05%, $MnSO_4.7 H_2O$, 0.0005%, $ZnSO_4.7 H_2O$, 0.001%, and $CaCl_2.2 H_2O$, 0.002%. The seed medium is inoculated with spores from ¼YME agar medium and incubated for 42–48 hours at 25° C. on a rotary shaker operating at 220 rpm. A 1.0 ml aliquot of the resulting seed culture is used to inoculate a 250 ml non-baffled Erlenmeyer flask containing production medium prepared with distilled water and which consists of Ardamine PH, 3%, MOPS, 1%, glucose 7.5% and $CaCO_3$, 0.1% where the pH is adjusted to 6.8 with NAOH prior to autoclaving. The production culture is incubated for 168 hours at 25° C. on a rotary shaker operating at 220 rpm. A methanol extraction is achieved by addition of an equal volume of methanol to the broth culture, agitating at high speed on an Eberbach reciprocating shaker for 30 minutes followed by centrifugation. The aqueous methanolic extracts are analyzed by TLC and HPLC.

By reverse phase HPLC (Whatman Partisil 5 ODS-3, 0.1% aqueous $H_3PO_4$:$CH_3CN$, 40:60, 1 ml/min, 60° C.), the major component of the subject culture has a retention time of 9.25 minutes relative to 14.8 minutes for FK-506. This component has the same retention time by HPLC and the same $R_f$ by TLC as 3 1 -desmethyl-L-679,934 (L-682,993).

For structure determination, the compound is isolated on a semi-preparative reverse phase octadecyl $C_{18}$ HPLC column (Whatman Magnum 9, Partisil 10 ODS-3). Six shake flasks of the mutant are extracted with an equal volume of methanol, centrifuged, and the supernatant evaporated to remove the methanol. The resulting aqueous phase is extracted twice with methylene dichloride and evaporated to dryness under a stream of nitrogen. The residue is resuspended in methanol and an aliquot is injected onto the semipreparative column. The solvent system is $H_2O$:$CH_3CN$ (40:60) at ambient temperature and a flow rate of 3 ml/min. The broad peak eluting between 10 and 13 minutes is collected, evaporated under a stream of nitrogen and resuspended in 1 ml of methanol. The concentration of the sample is estimated by analytical HPLC to be approximately 2 mg/ml. NMR analysis (see FIGURE) determines that the compound produced by the mutant strain is the same as C-31 desmethyl FK-506 as described in U.S. Pat. No. 4,981,792.

It is reasonably believed that a mutation in the FK-506 C-31 O-methyltransferase gene is inactivated resulting in the efficient production of C-31 desmethyl FK-506. It is further noted that O-methylation at C-13 and C-15 is not affected, indicating that a different protein or proteins, is responsible for the O-methylation at these positions in C-31 desmethyl FK-506 and FK-506.

What is claimed is:

1. A process for producing the immunosuppressant demethomycin (L-682,993), comprising culturing Streptomyces sp. ATCC No. 55334 under submerged aerobic fermentation conditions in an aqueous nutrient medium containing assimilable sources of carbon and nitrogen for a sufficient time to produce the demethomycin, and recovering the demethomycin from the medium.

* * * * *